US00PP16643P2

(12) United States Plant Patent
Utecht

(10) Patent No.: US PP16,643 P2
(45) Date of Patent: Jun. 13, 2006

(54) ***GERANIUM* PLANT NAMED 'FILUN'**

(50) Latin Name: *Pelargonium peltatum*
Varietal Denomination: Filun

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 83 days.

(21) Appl. No.: 10/998,667

(22) Filed: Nov. 30, 2004

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

German PBR Application No. PEL 1891 filed Jun. 4, 2003 and withdrawn Oct. 5, 2004 (Copy of German Gazettes dated 1) Jul. 15, 2003—Listing Assigned Application for Protection Number (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3895 filed Nov. 21, 2003 (Copy of Canadian Plant Varieties Journal dated Jan., 2004 Listing Assigned Application Number (2 pgs).

Community Plant Variety Office (CPVO) No. 2004/1249 filed Jul. 5, 2004 (Copy of Official Gazette of the CPVO dated Oct. 15, 2004 Listing Assigned Application Number and Variety Denomination (3 pgs).

Fischer 2005 catalogue offering 'Filun' (with shipment of plant material available starting Dec., 2004) (3 pgs).

*Primary Examiner*—Kent L. Bell
(74) *Attorney, Agent, or Firm*—Foley & Lardner LLP

(57) ABSTRACT

A new and distinct cultivar of *geranium* plant named 'Filun', particularly characterized by the combined features of white to pale pink, double-type flowers; large inflorescences; green foliage with slight zonation; well branching and good rooting habits; moderately vigorous growth habit; initially round and bushy, and later, long, trailing plant habit; and mid to late spring flowering response.

1 Drawing Sheet

Genus and species of the plant claimed: *Pelargonium peltatum* L'Héritier (hybrid).
Variety denomination: 'Filun'.

BACKGROUND OF THE INVENTION

The present invention comprises a new and distinct cultivar of *geranium*, botanically known as *Pelargonium peltatum,* and hereinafter referred to by the cultivar name 'Filun'.

'Filun' is a product of a planned breeding program which had the objective of creating new ivy *geranium* cultivars with white, semi-double to double flower type, preferably zoned foliage, medium growth habit, and good propagation and rooting characteristics.

'Filun' originated from a hybridization made by the inventor, Angelika Utecht, in a controlled breeding program in Hillscheid, Germany, in 1997. The female parent was the unpatented hybrid plant no. 95-415-22, having very light violet, single-type flowers and medium green foliage with zonation. The male parent of 'Filun' was the patented variety 'Fislunova' (U.S. Plant Pat. No. 12,329), which is characterized by white, semi-double flowers, foliage with slight zonation, and relatively compact plant habit.

'Filun' was selected as one flowering plant within the progeny of the stated cross by Angelika Utecht in 1998 in a controlled environment in Moncarapacho, Portugal.

The first act of asexual reproduction of 'Filun' was accomplished when vegetative cuttings were taken from the initial selection in the fall of 1998 in a controlled environment in Moncarapacho, Portugal, by, or under the supervision of, Angelika Utecht.

Horticultural examination of plants grown from cuttings of the plant initiated in May of 1999 in Hillscheid, Germany, and continuing thereafter, has demonstrated that the combination of characteristics as herein disclosed for 'Filun' are firmly fixed and are retained through successive generations of asexual reproduction.

BRIEF SUMMARY OF THE INVENTION

'Filun' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Filun' in combination distinguish this *geranium* as a new and distinct cultivar:

1. white to very light pink flowers, with distinct red-purple markings;
2. large, double flowers and large inflorescences;
3. deep green foliage with weak zonation;
4. well-branched, trailing plant habit and moderately vigorous growth;
5. mid to late spring flowering response; and
6. good rooting characteristics.

Of the many commercial cultivars known to the present inventor, the most similar is the parental variety 'Fislunova'.

In comparison to 'Fislunova', with pure white main flower color, 'Filun' has white to occasionally pale pink colored flowers, with more distinct red markings. 'Filun' has somewhat bigger inflorescences and grows generally more vigorously. The main advantage of 'Filun', however, lies in that its cuttings develop roots better and faster.

BRIEF DESCRIPTION OF THE DRAWING

The accompanying photographic drawing shows typical flower and foliage characteristics of 'Filun' with colors being as true as possible with an illustration of this type. The photographic drawing shows a side perspective view of a flowering 'Filun' plant in a hanging basket with leaves, buds and inflorescences.

DETAILED BOTANICAL DESCRIPTION

The measurements were taken in Hillscheid, Germany, in mid May 2003, 15 weeks after planting of rooted cuttings. The plants were growing in 14 cm pots; they had been pinched once.

In the following description, color references are made to The Royal Horticultural Society Colour Chart. The color values were determined indoors from plants growing in a green-house in May 2003, in Hillscheid, Germany.

Parentage:
- *Male parent.*—'Fislunova' (U.S. Plant Pat. No. 12,329).
- *Female parent.*—Unpatented, hybrid plant no. 95-415-22.

Classification: *Pelargonium peltatum* L'Héritier (hybrid).
Propagation: Vegetative cuttings.
Inflorescence:
Umbel:
- *Shape.*—Irregular to nearly semi-spherical.
- *Average diameter.*—108 mm.
- *Average depth.*—50 mm.
- *Number of flowers per umbel.*—Usually 8–10.

Peduncle:
- *Peduncle size.*—173 mm in length, 3 mm in diameter.
- *Peduncle color.*—Light green, RHS 143 C.

Pedicel:
- *Pedicel length.*—39 mm in length, with a spur at the lower end.
- *Pedicel diameter.*—3 mm, relatively thick.
- *Pedicel color.*—Mainly green, RHS 143 B, partly brown (greyed-orange), RHS 176 C.

Corolla:
- *Average length.*—56–58 mm.
- *Average width.*—53–54 mm.
- *Depth.*—20 mm.
- *Form.*—Double-type.
- *Shape.*—Oval outline, often with a gap between upper and lower petals.

Petaloids:
- *Number of petaloids.*—3–5.
- *Length.*—Variable, maximum length is 15 mm.
- *Width.*—Variable, ranges from 2 to 8 mm.
- *Overall shape.*—Irregular, filiform to narrow elliptical, distinctly narrower and somewhat shorter than the petals.
- *Apex shape.*—Acute or rounded.
- *Base shape.*—Attenuate.
- *Margin.*—Entire.
- *Color of upper petaloids.*—White, RHS 155 D.
- *Color of lower petaloids.*—White, RHS 155 D.

Petals:
- *Number of petals.*—10–15.
- *Shape of petals.*—Obovate, base attenuate, upper end rounded to truncate, margin is usually entire.
- *Size of petals.*—Upper petals: 35 mm long, 20–23 mm wide. Lower petals: 29–30 mm long, 21–22 mm wide.
- *Color (general tonality from a distance of three meters).*—White to pale light pink.
- *Color of upper petals.*—From pure white, lighter than RHS 155 D, to red-purple RHS 69 C.
- *Markings of upper petals.*—2 dark red-purple veins, RHS N66B and a small spot, red-purple, RHS N66A.
- *Color of lower petals.*—White, lighter than RHS 155 D, to pale pink, RHS 65 D.
- *Markings of lower petals.*—None.
- *Color of lower surface of petals.*—From white, RHS 155 D, to red-purple, RHS 69 C.

Sepals:
- *Color of sepals.*—Both surfaces: light green, RHS 143 B to 143 C; largest sepal with infusion of brown (greyed-orange), RHS 176 D.
- *Number of sepals.*—5, occasionally 6.
- *Shape of sepals.*—Linear to ensiform, acute tip, base, surface with weak pubescence, margin entire.
- *Size of sepals.*—15 mm long, 5–6 mm wide for the largest upper sepal, 4 mm in width for the other sepals.

Bud: (just prior to petals unfolding).
- *Shape.*—Elliptical.
- *Color of sepals.*—Light green, RHS 143 B.
- *Color of petals.*—Yellow-white, RHS 158 B.
- *Length.*—18 mm.
- *Width.*—10 mm.

Reproductive organs:
- *Androecium.*—5–7 fertile anthers, moderate pollen, orange, RHS 28 A, filaments white, RHS 155 D, to light-pink, RHS 52 D.
- *Gynoecium.*—One pistil, whitish style, RHS 155 D to red-purple, 65 D, stigma 5–6-lobed stigma, red, RHS 53 D.
- *Fertility/seed set.*—Seed set may occur, mainly from late summer to fall.
- *Fruit.*—Oblong, about 6 mm wide, rostrum (beak) 38–42 mm long.
- *Seed.*—Oblong, 4–5 mm long, brown (greyed-orange), RHS 177 B.

Spring flowering response period: In Hillscheid, Germany, in 2003 plants had on average 0.2 flowers opened 12 weeks after planting of rooted cuttings (pinched plants).

Outdoor flower production: Continuously and moderately rich flowering, the flower count in 2003 in Hillscheid, Germany, indicated about 25 inflorescence per plant in late summer.

Durability: Good stability of flower color, fair rain resistance.

Lastingness of the individual flower: About 8–9 days at 18° C.

Fragrance: None.

Plant:

Foliage:
- *Shape.*—Weakly ivy-shaped, apex almost round with only very weak lobes, cordate base, with the gap between the lowest lobes closed to overlapping.

*Margin.*—Entire, almost flat, hardly wavy.

*Texture.*—Upper surface smooth, somewhat glossy, weak pubescence.

*Size of leaf.*—91 mm wide, about 55 mm long.

*Color of upper surface.*—Medium green, between RHS 137 C and 143 A.

*Color of zonation.*—Brown (greyed-orange), closest to RHS 166 A, the shape is a small ring of relatively weak distinctness.

*Color of lower surface.*—Green, RHS 143 B.

*Petiole.*—About 50 mm long, 2–3 mm diameter, light green in color, closest to RHS 143 C.

General appearance and form:

*Stem color.*—Light green, RHS 143 B.

*Internode length.*—50–70 mm.

*Branching pattern.*—8.3 branches on average.

*Size of plants.*—Height: 20.5 cm (15 week-old plants, as described). Diameter: 33 cm (15 week-old plants, as described). Length: 25 cm (15 week-old plants); and 85 cm (30 week-old plants in hanging-baskets, around September 1), measured from the top of the soil (base of the main stem) to the tips of the branches, without inflorescences.

I claim:

1. A new and distinct cultivar of *geranium* plant named 'Filun', as described and illustrated herein.

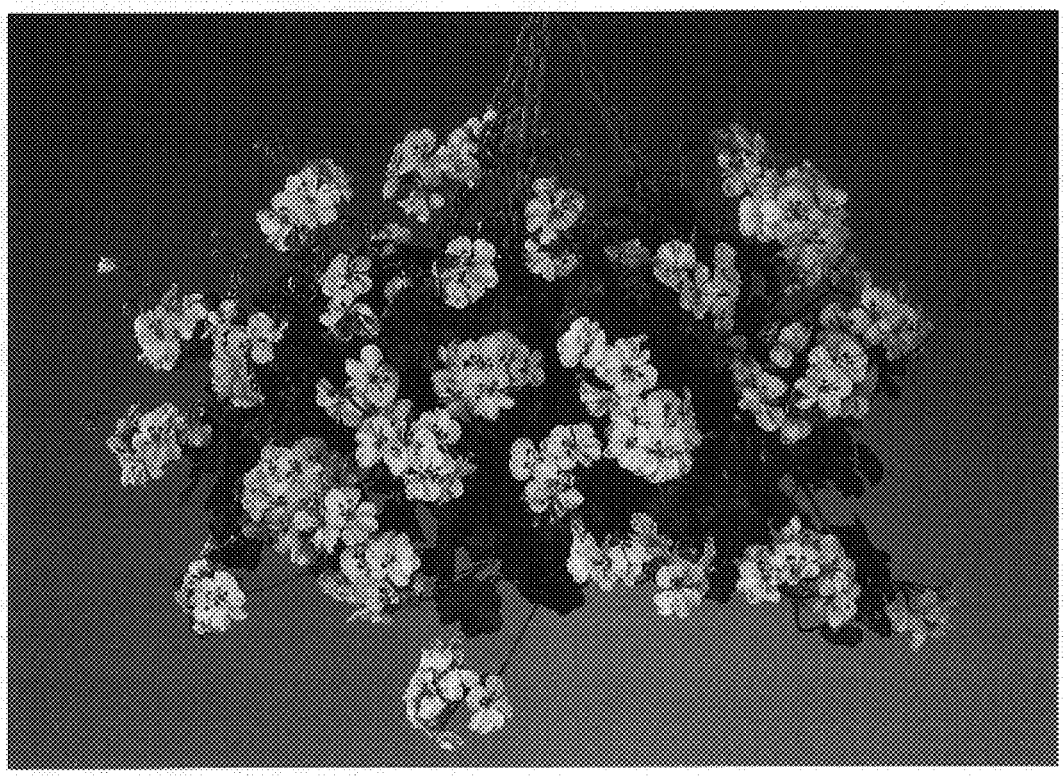

* * * * *